United States Patent [19]

DesMarais et al.

[11] Patent Number: 4,808,177
[45] Date of Patent: Feb. 28, 1989

[54] ABSORBENT ARTICLE HAVING FLOATING INNER CUFFS

[75] Inventors: Thomas A. DesMarais, Norwood; Robert H. Siegfried, Cincinnati, both of Ohio

[73] Assignee: The Procter & Gamble Company, Cincinnati, Ohio

[21] Appl. No.: 103,872

[22] Filed: Oct. 2, 1987

[51] Int. Cl.⁴ ............................................. A61F 13/16
[52] U.S. Cl. ................................ 604/385.1; 604/385.2
[58] Field of Search ................. 604/385.1, 385.2, 394, 604/396, 397, 399, 389

[56] References Cited

U.S. PATENT DOCUMENTS

| | | | |
|---|---|---|---|
| 3,860,003 | 1/1975 | Buell | 604/385.1 |
| 4,040,423 | 8/1977 | Jones, Sr. | 604/385.1 |
| 4,041,950 | 8/1977 | Jones, Sr. | 604/385.1 |
| 4,490,148 | 12/1984 | Beckstrom | 604/385.1 |
| 4,500,316 | 2/1985 | Damico | 604/389 |
| 4,643,728 | 2/1987 | Karami | 604/385.2 |
| 4,662,877 | 5/1987 | Williams | 604/385.2 |
| 4,695,278 | 9/1987 | Lawson | 604/385.2 |
| 4,704,116 | 11/1987 | Enloe | 604/385.2 |

FOREIGN PATENT DOCUMENTS 2159693 12/1985 United Kingdom ............. 604/385.2

*Primary Examiner*—James C. Yeung
*Attorney, Agent, or Firm*—Steven W. Miller; John M. Pollaro; Fredrick H. Braun

[57] ABSTRACT

An integral disposable absorbent article such as a diaper having an absorbent core, a backsheet, a continuous topsheet, an elastically contractible leg cuff along each longitudinal edge, and a pair of floating inner cuffs extending longitudinally along the absorbent article in at least the crotch region. The floating inner cuffs provide enhanced containment of body exudates and enhanced fit. The floating inner cuffs each preferably comprise a cuff layer, a base layer underlaying the cuff layer, a first seam that affixes a portion of the cuff layer to the base layer, a central seam that affixes another portion of the cuff layer to the base layer, an unadhered stand-up portion of the cuff layer between the first seam and the central seam, and a central elastic member having a pair of affixed portions and an unaffixed portion between the pair of affixed portions. The gathering action of the central elastic member causes both the unaffixed portion and the unadhered stand-up portion of the cuff layer to stand-up and be spaced away from the base layer to provide a ridge that contains body exudates. Since the unaffixed portion of the central elastic member is not affixed to the cuff layer or the base layer, the central elastic member is free to move or float within the floating inner cuff so that it may seek and be positioned adjacent the leg crease of the wearer to optimize fit and enhance containment.

25 Claims, 2 Drawing Sheets

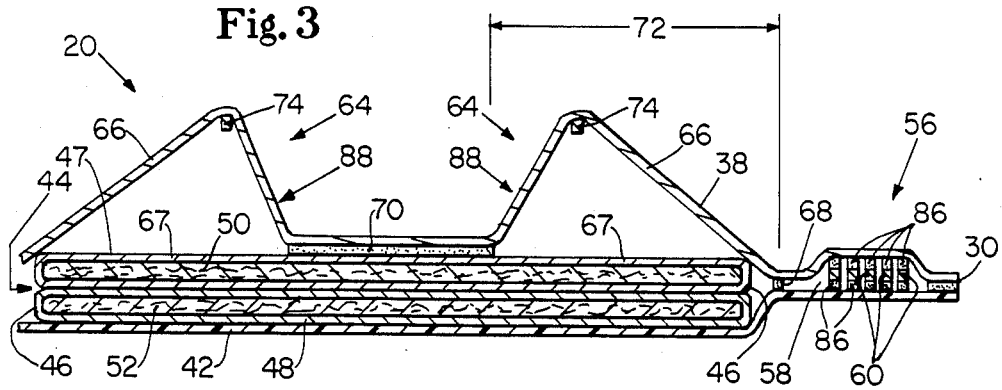
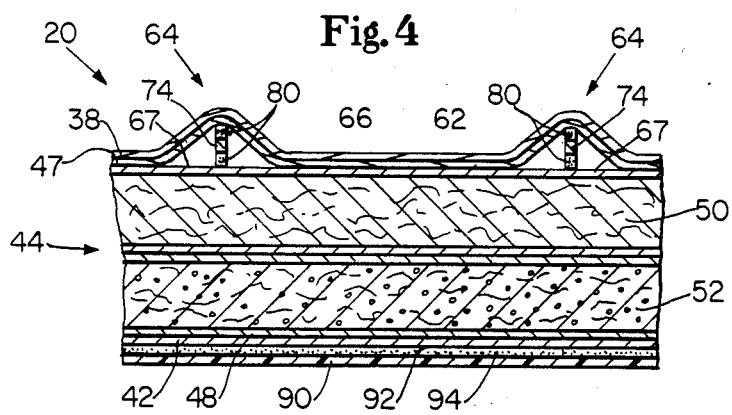

ABSORBENT ARTICLE HAVING FLOATING INNER CUFFS

FIELD OF THE INVENTION

The present invention relates to absorbent articles such as disposable diapers, and more particularly, to absorbent articles having elastically contractible leg cuffs and a pair of floating inner cuffs positioned inboard of the leg cuffs to provide improved containment characteristics.

BACKGROUND OF THE INVENTION

The major function of absorbent articles, such as disposable diapers and adult incontinent briefs, is to absorb and contain body exudates. Such articles are intended to prevent body exudates from soiling, wetting, or otherwise contaminating clothing or other articles, such as bedding, that come in contact with the wearer. The most common mode of failure for such products occurs when body exudates leak out of the gaps between the absorbent article and the wearer's leg or waist to adjacent clothing because they are not immediately absorbed within the article. This is most evident with loose fecal material which is not easily absorbed by the absorbent article and tends to "ride" on the top surface of the absorbent article.

Contemporary disposable diapers, such as those disclosed in U.S. Pat. No. 3,860,003 issued to Kenneth Barclay Buell on Jan. 14, 1975, have a topsheet, a backsheet, an absorbent core, and elasticized leg flaps to improve both wearing comfort and the ability to contain body exudates. These elasticized leg flaps prove effective generally to prevent wicking and overflow from the fluid laden diaper to clothing contacting the edges of the diaper in that the elasticized leg flaps present a fluid impervious barrier between the edge of the diaper and the contacting clothing, and in addition, provide a gasketing action about the legs of the wearer. Despite the effectiveness of such structures, however, body exudates can leak through the elasticized leg flaps and soil the wearer's clothing because the diaper does not constrain the free flow of such material nor provide a structure to hold it within the diaper so that as such material freely flows on the top surface of the topsheet, it tends to work its way past the elasticized leg flaps.

Therefore, it is an object of the present invention to provide an absorbent article which has improved containment characteristics.

It is an additional object of the present invention to provide an absorbent article having a pair of central elastic members which act to enhance the containment of body exudates.

It is also an object of the present invention to provide an absorbent article having floating inner cuffs that are free standing to provide a raised surface on the topsheet when the absorbent article is fitted on the wearer such that a ridge is formed which contains and holds body exudates within the absorbent article.

It is a further object of the present invention to provide an absorbent article having elastically contractible leg cuffs and a pair of floating inner cuffs formed from the central elastic members so as to provide a dual restraint against the leakage of body exudates, thereby improving the containment characteristics of the absorbent article.

It is a still further object of the present invention to provide an absorbent article have improved positioning of the topsheet relative to the genital area of the wearer.

It is an even further object of the present invention to provide an absorbent article having improved fit by providing central elastic members that are floating such that they "seek" the leg crease of the wearer to provide a sustained tighter fit on the wearer since the central elastic members are free to move and adapt to the wearer's body. The improved fit of the absorbent article further enhances the containment characteristics of the absorbent article.

These and other objects of the invention will be more readily apparent when considered in reference to the following description and when taken in conjunction with the accompanying drawings.

SUMMARY OF THE INVENTION

In accordance with the present invention, an integral disposable absorbent article such as a diaper is provided with an absorbent core, a backsheet associated with the absorbent core on the garment facing surface, a continuous topsheet associated with the absorbent core on the body facing surface, a side flap extending outwardly from and along each side edge of the absorbent core, a flap elastic member operatively associated with each side flap to form an elastically contractible leg cuff, and a pair of floating inner cuffs. Each of the floating inner cuffs preferably comprises a cuff layer, a base layer underlaying the cuff layer, a first seam for affixing a portion of the cuff layer to the base layer, a central seam for affixing a portion of the cuff layer to the base layer, an unadhered stand-up portion of the cuff layer positoned between the first seam and the central seam, and a central elastic member preferably positioned subjacent the unadhered stand-up portion of the cuff layer. The central elastic members have a pair of affixed portions and an unaffixed portion that is preferably not affixed to the absorbent article in at least the crotch region so as to space both the cuff layer and the central elastic member away from the base layer and allow the central elastic member to "float" in the crotch region. A ridge is formed between the cuff layer and the base layer in at least the crotch region because the cuff layer is spaced away from the base layer. When a diaper embodiment of the present invention is applied to a wearer, the central elastic members float and preferably ride up along the inner creases of the leg of the wearer in the crotch region. Leakage prevention is enhanced because body exudates which are not immediately absorbed by the absorbent core contact the ridges and are contained and held within the central portion of the diaper until the body exudates are either absorbed by the absorbent core of the diaper is removed from the wearer such that the body exudates are not likely to leak out of the diaper at the gaps between the diaper and the legs of the wearer. Further, the sustained fit provided by the "floating" central elastic members also enhances containment.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

FIG. 3 is a fragmentary sectional view taken along section line 3—3 of FIG. 2.

FIG. 4 is a fragmentary sectional view taken along section line 4—4 of FIG. 2.

DETAILED DESCRIPTION OF THE INVENTION

As used herein, the term "integral disposable absorbent article" refers to articles which absorb and contain body exudates and more specifically refers to articles which are placed against or in proximity to the body of the wearer to absorb and contain the various exudates discharged from the body, and which are intended to be discarded after a single use (i.e., they are not intended to be laundered or otherwise restored or reused), and which are of a unitary-type construction in that they do not require separate manipulative parts like a separate holder and liner. A preferred embodiment of the integral disposable absorbent article of the present invention, diaper 20, is shown in FIGS. 1-4. As used herein, the term "diaper" refers to a garment generally worn by infants and incontinent persons that is worn about the lower torso of the wearer. It should be understood, however, that the present invention is also applicable to other integral disposable absorbent articles such as incontinent undergarments and the like.

Figure 1:
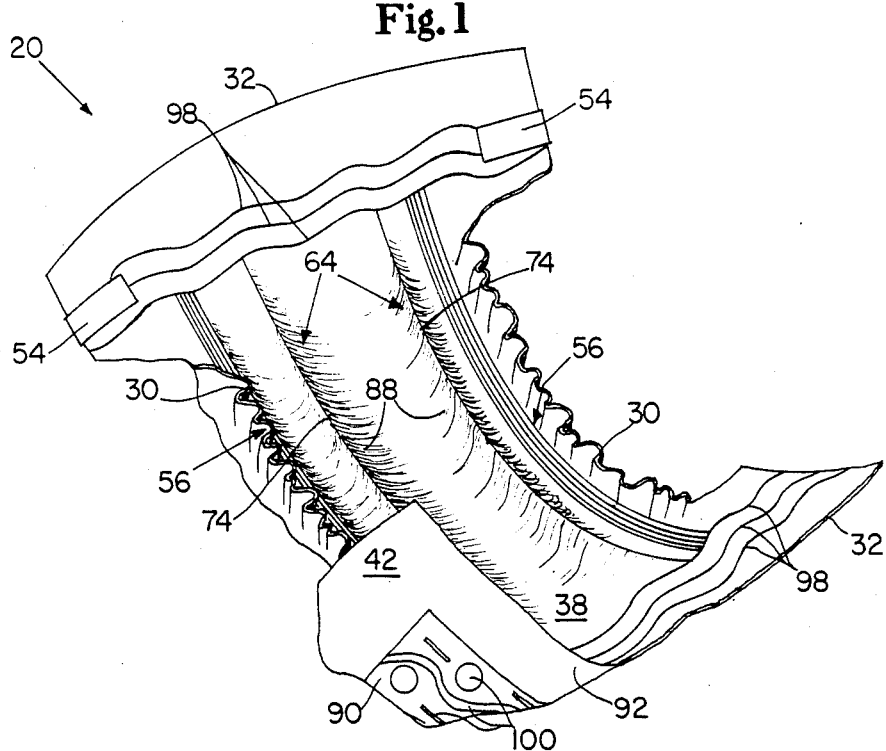
FIG. 1 is a perspective view of a disposable diaper embodiment of the present invention.
Figure 2:
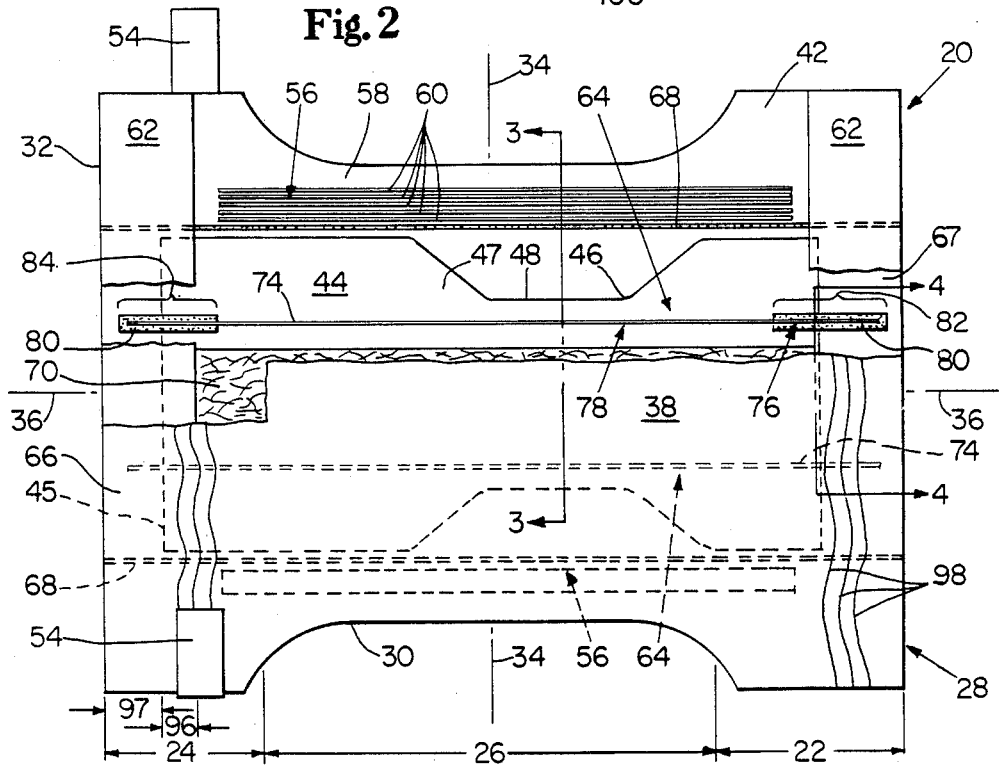
FIG. 2 is a plan view of a disposable diaper embodiment of the present invention having portions cut-away to reveal underlying structure.

FIG. 1 is a perspective view of the diaper 20 of the present invention. FIG. 2 is a plan view of the diaper 20 of the present invention in its flat-out, uncontracted state (i.e., with all elastic induced contraction pulled out) with portions of the structure being torn away to more clearly show the construction of the diaper 20 and with the portion of the diaper which contacts the wearer facing the viewer. The diaper 20 is shown in FIG. 2 to have a front waist region 22, a back waist region 24, a crotch region 26 and a periphery 28 which is defined by the outer edges of the diaper in which the longitudinal edges are designated 30 and the end edges are designated 32. The diaper 20 additionally has a lateral centerline which is designated 34 and a longitudinal centerline which is designated 36.

The diaper 20 preferably comprises a continuous topsheet 38; a backsheet 42; an absorbent core 44 having end edges 45, side edges 46, a body facing surface 47 and a garment facing surface 48 and preferably comprising a dual-layer absorbent core comprising an upper layer 50 and a lower layer 52; a pair of tape-tab fasteners 54; elastically contractible leg cuffs 56 each comprising a side flap 58 and one or more, preferably a plurality of, flap elastic members 60; a waistshield 62 positioned in each of the front waist region 22 and the back waist region 24; and a pair of floating inner cuffs 64. The floating inner cuffs 64 are shown to preferably each comprise a cuff layer 66 preferably comprising a portion of the topsheet 38; a base layer 67 underlaying the cuff layer 66 and preferably comprising the underlying structure of the diaper 20 such as the backsheet 42, the absorbent core 44 or the waistshields 62; a first seam 68 for affixing the cuff layer 66 to the base layer 67; a central seam 70 for affixing the cuff layer 66 to the base layer 67; and unadhered stand-up portion 72 of the cuff layer 66 positioned between the first seam 68 and the central seam 70; and a central classic member 74 preferably positioned subjacent the unadhered stand-up portion of the cuff layer 66 (i.e., between the first seam 66 and the central seam 70 and between the cuff layer 66 and the base layer 67). The central elastic members 74 are operatively associated with the floating inner cuff 64 in an elastically contractible condition at a pair of fixed portions 76. An unaffixed portion 78 is positioned between the pair of fixed portions 76. The unaffixed portion 78 of the central elastic member 74 is preferably not affixed to either the cuff layer 66 or the base layer 67 in at least the crotch region 26 to form a ridge 88 as is shown in FIG. 1. The diaper 20 additionally comprises adhesive attachment means 80 for affixing each of the fixed portions 76 of the central elastic members 74 to the cuff layer 66 and the base layer 67, preferably to the waistshields 62 and a portion of the absorbent core 44. The areas in which the adhesive attachment means 80 are disposed are designated front zone 82 and back zone 84. As shown in FIG. 1, the diaper 20 additionally preferably comprises a stiffening means 90 positioned on the outside surface 92 of the backsheet 42 in the front waist region 22, indicia means 100 positioned on the stiffening means 90, and leakage migration resistant segments 98 in the topsheet 38 corresponding to each waistshield 62. While the topsheet 38, the absorbent core 44, the backsheet 42, the side flaps 58, and the flap elastic members 60 may be assembled in a variety of well known configurations, a preferred diaper configuration is described generally in U.S. Pat. No. 3,860,003 entitled "Contractable Side Portions for Disposable Diaper", which issued to Kenneth Barclay Buell on Jan. 14, 1974, and which patent is incorporated herein by reference.

FIG. 2 shows a preferred embodiment of the diaper 20 in which the topsheet 389 and the backsheet 42 are coextensive and have length and width dimensions generally larger than those of the absorbent core 44. The topsheet 38 is associated with and superposed on the backsheet 42 to thereby form the periphery 28 of the diaper 20. The periphery 28 defines the outer perimeter or, in other words, the edges of the diaper 20. The periphery 28 comprises the end edges 32 and the longitudinal edges 30.

The diaper 20 has front and back waist regions 22 and 24 extending, respectively, from the end edges 32 of the diaper periphery 28 toward the lateral centerline 34 of the diaper 20 a distance from about 1/5 to about ⅓ the length of the diaper 20. The waist regions comprise these portions of the diaper 20 which, when worn, encircle the waist of the wearer. The crotch region 26 is that portion of the diaper 20 between the waist regions 22 and 24, and comprises that portion of the diaper 20 which, when worn, is positioned between the legs of the wearer and covers the lower torso of the wearer.

FIG. 3 is a fragmentary sectional view taken along line 3—3 of FIG. 2 and depicts the preferred diaper construction in the crotch region 26 of the diaper 20. The absorbent core 44 comprises an upper layer 50 and a lower layer 52, each of the upper layer 50 and the lower layer 52 comprising an absorbent layer completely enveloped by tissue layers. The absorbent core 44 has a side edge 46, a body facing surface 47, and a garment facing surface 48. The continuous topsheet 38 is associated with the absorbent core 44 on the body facing surface 47. The backsheet 42 is associated with the absorbent core 44 on the garment facing surface 48. Both the topsheet 38 and the backsheet 42 extend beyond the side edge 46 of the absorbent core 44 to define the side flap 58. The topsheet 38 and the backsheet 42 thus enclose the flap elastic members 60 adjacent the longitudinal edge 30 in the periphery 28. The flap elastic members 60 are operatively associated with the topsheet-backsheet formed side flap 58 by elastic attachment means 86 to to form an elastically contractible leg cuff 56. The floating inner cuffs 64 are shown in FIG. 3 to each comprise a cuff layer 66 preferably formed from a portion of the topsheet 38; a base layer 67 underlaying the cuff layer 66 and preferably comprising the absorbent core 44 and the portion of the backsheet 42 extending beyond the side edges 46 and the end edges 45 of the absorbent core 44; a first seam 68 positioned inboard of the flap elastic members 60, preferably between the flap elastic members 60 and the side edge 46 of the absorbent core 44, to secure the cuff layer 66, preferably the topsheet 38, to the base layer 67, preferably the backsheet 42; a central seam 70 spaced inboard from the first seam 68 to secure the cuff layer 66, preferably the topsheet 38, to the base layer 67, preferably the absorbent core 44; an unadhered stand-up portion 72 of the cuff layer 66 positioned between the first seam 68 and the central seam 70; and a central elastic member 74 positioned subjacent the unadhered stand-up portion 70 of the cuff layer 66. (The term "inboard" is defined as the direction toward the particular centerline of the diaper 20 that is parallel to the respective edge of the diaper 20 along which the flap elastic members 60 are disposed.) As shown in FIG. 3, the unaffixed portion 78 of the central elastic member 74 is positioned in the crotch region 26 and is preferably not affixed to the base layer 67, or any other element of the diaper 20 such that the gathering action of the central elastic member 74 causes the central elastic member 74 to be spaced away from the base layer 67, preferably the absorbent core 44, such that the unadhered stand-up portion 72 of the cuff layer 66 stands-up and is spaced away from the base layer 67 to thereby form a ridge 88 to constrain, contain and hold body exudates within the diaper 20. The unaffixed portion 78 of the central elastic member 74 is also preferably not affixed to the cuff layer 66 so that the central elastic member 74 is free to move or float within the floating inner cuff 64 so that it may seek and be positioned adjacent the leg crease of the wearer so as to provide an optimized fit that enhances containment of body exudates.

FIG. 4 is a fragmentary sectional view taken along line 4—4 of FIG. 2 and depicts the diaper construction in the front waist region 22 of the diaper 20. (It should be understood that the diaper construction in the back waist region 24 is preferably identical to the construction in the front waist region 22 except as discussed herein.) The absorbent core 44 comprises an upper layer 50 and a lower layer 52, each of the upper layer 50 and the lower layer 52 comprising an absorbent layer completely enveloped by tissue layers. The absorbent core 44 has a side edge 46, a body facing surface 47, and a garment facing surface 48. The continuous topsheet 38 is associated with the absorbent core 44 on the body facing surface 47. The backsheet 42 is associated with the absorbent core 44 on the garment facing surface 48. Although not shown in FIG. 4, it should be understood from FIG. 2 that both the topsheet 38 and the backsheet 42 extend beyond the side edge 46 of the absorbent core 44 to define the side flap 58, and that the flap elastic members 60 preferably do not extend into the waist regions. A waistshield 62 is positioned between the topsheet 38 and the absorbent core 44. The floating inner cuffs 64 are shown in FIG. 4 to comprise a cuff layer 66 preferably comprising a portion of the topsheet 38 and the waistshield 62 in the waist regions; a base layer 67 underlaying the cuff layer 66 and preferably comprising the absorbent core 44 and the portion of the backsheet 42 extending beyond the side edges 46 and the end edges 45 of the absorbent core 44 in the waist regions; an unadhered stand-up portion 72 of the cuff layer 66; and a central elastic member 74 positioned subjacent the unadhered stand-up portion 72 of the cuff layer 66. Each of the floating inner cuffs 64 also comprise a first seam for securing a portion of the cuff layer 66 to the base layer 67; the first seam not being shown in FIG. 4. While each of the floating inner cuffs 64 may additionally comprise a central seam positioned in the waist regions, as shown in FIG. 4 the central seam preferably does not extend completely through the waist regions. The affixed portion 76 of the central elastic members 74 is positioned in the front waist region 22 and is affixed to both the cuff layer 66, preferably the waistshield 62, and the base layer 67, preferably the absorbent core 44 by an elastic attachment means 80. Therefore, the fixed portion 76 of the central elastic member 74 is constrained from standing-up and being spaced away from the base layer 67 or from providing a floating member for enhanced fit. The fixed portion 76, however, provides comfort for the wearer in the waist regions in that the central elastic members 74 lie flat against the waist of the wearer. In the preferred embodiment shown in FIG. 4, the diaper additionally comprises a stiffening means 90 for stiffening the backsheet 42 of the diaper 20 so as to prevent the central elastic members 74 from causing the waist to sag because the front waist region 22 is pulled downwardly by the gathering action of the central elastic members 74. The stiffening means 90 is preferably positioned on the outside surface 92 of the backsheet 42 in preferably only the front waist region 22, and is secured to the backsheet 38 by preferably an adhesive layer 94.

The topsheet 38 of the diaper 20 of the present invention is compliant, soft feeling, and non-irritating to the wearer's skin. Further, the topsheet 38 is liquid pervious permitting fluids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of hydrophobic material to isolate the wearer's skin from fluids retained in the absorbent core 44.

A particularly preferred topsheet 38 comprises staple length polypropylene fibers having a denier of about 1.5, such as Hercules Type 151 polypropylene fibers marketed by Hercules, Inc. of Wilmington, Del. As used herein, the term "staple length fibers" refers to those fibers having a length of at least about 15.9 mm (0.625 inches).

There are a number of manufacturing techniques which may be used to manufacture the topsheet 38. For example, the topsheet 38 may be woven, non-woven, spunbonded, carded, or the like. A preferred topsheet 38 is carded, and thermally bonded by means well known to those skilled in the fabrics art. Preferably, the topsheet 38 has a weight of from about 18 to about 25 grams per square meter, a minimum dry tensile strength of at least about 400 grams per centimeter in the machine direction and a wet tensile strength of at least about 55 grams per centimeter in the cross machine direction.

The topsheet 38 is also preferably continuous. As used herein, the term "continuous topsheet" means a topsheet 38 that does not have large apertures or discontinuities in the material. Thus, while the topsheet 38 may be manufactured from a material such as a formed film having minute apertures for acquiring liquids, the topsheet 38 should not have apertures more than about 2.5 cm (about 1 inch) in diameter.

The absorbent core 44 may be any means which is generally compressible, conformable, non-irritating to the wearer's skin, and capable of absorbing and retaining liquids and certain body exudates. The absorbent core 44 has end edges 45, side edges 46, a body facing surface 47, and a grament facing surface 48. A preferred absorbent core 44 comprises an upper layer 50 and a lower layer 52, the upper surface of the upper layer 50 defining the body facing surface 47 and the lower surface of the lower layer 52 defining the garment facing surface 48.

The absorbent core 44 may be manufactured in a wide variety of sizes and shapes (e.g., rectangular, hourglass, asymmetric etc.) and from a wide variety of liquid absorbent materials commonly used in disposable diapers and other absorbent articles, such as comminuted wood pulp which is generally referred to as airfelt. Examples of other suitable absorbent material include creped cellulose wadding, absorbent foams, absorbent sponges, super absorbent polymers, absorbent gelling materials, or any equivalent material or combination of materials. The total absorbent capacity of the absorbent core should, however, be compatible with the design exudate loading in the intended use of the diaper 20. Further, the size and absorbent capacity of the absorbent core 44 may be varied to accommodate wearers ranging from infants through adults.

While the absorbent core 44 may comprise a single layer of absorbent material such as the configuration described in U.S. Pat. No. 4,610,678 entitled "High-Density Absorbent Structures" which issued to Paul T. Weisman and Stephen A. Goldman on Sept. 9, 1986, and which is incorporated herein by reference, a preferred embodiment of the absorbent core 44 shown in FIGS. 2-4 is a dual-layered absorbent core in a preferred configuration such as is generally described in U.S. Pat. No. 4,673,402 entitled "Absorbent Article with Dual-Layered Cores" which issued to Paul T. Weisman, Dawn I. Houghton and Dale A. Gellert on June 16, 1987, and which is incorporated herein by reference, having an asymmetric-shaped upper layer 50 and a lower layer 52. The upper layer 50 preferably acts as a liquid acquisition/distribution layer comprised primarily of hydrophilic fiber material. The lower layer 52 acts as a fluid storage layer comprised of a mixture of hydrophilic fiber material and particles of an absorbent gelling material (hydrogel material). Each of the upper layer 50 and the lower layer 52 preferably comprises an absorbent layer encased in a tissue layer such as is shown in FIGS. 3 and 4. It should be understood, however, that the size, shape, configuration, and total absorbent capacity of the upper layer 50 or the lower layer 52 may be varied to accommodate wearers ranging from infants through adults. Therefore, the dimensions, shape, and configuration of both the upper layer 50 and the lower layer 52 may be varied (e.g., the upper layer or the lower layer may have a varying caliper, a hydrophilic gradient, a rapid acquisition zone or may contain superabsorbent materials).

The absorbent core 44 is superposed on the backsheet 42 and is preferably associated thereto by any attachment means (not shown) such as those well known in the art. For example, the absorbent core 44 may be secured to the backsheet 42 by a uniform continuous layer of adhesive, a patterned layer of adhesive, or an array of separate lines or spots of adhesive. An adhesive which has been found to be satisfactory is preferably a hot melt adhesive such as manufactured by Eastman Chemical Products Company of Kingsport, Tenn. and marketed under the tradename of Eastobond A-3 or Century Adhesives, Inc., of Columbus, Ohio and marketed under the tradename Century 5227. The attachment means preferably comprises an open pattern network of filaments of adhesive as is shown in U.S. Pat. No. 4,573,986 entitled "Disposable Waste-Containment Garment", which issued to James A. Minetola and David R. Tucker on Mar. 4, 1986, and which is incorporated herein by reference.

The backsheet 42 is impervious to liquids and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Preferably, the backsheet 42 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 42 is preferably embossed and/or matte finished to provide a more clothlike appearance. Further, the backsheet 42 may permit vapors to escape from the absorbent core 44 while still preventing exudates from passing through the backsheet 42.

The size of the backsheet 42 is dictated by the size of the absorbent core 44 and the exact diaper design selected. In a preferred embodiment, the backsheet 42 has a modified hourglass shape extending beyond the absorbent core 44 a minimum distance of at least about 1.3 cm to about 2.5 cm (about 0.5 to about 1.0 inch) around the entire diaper periphery 22.

The topsheet 38 and the backsheet 42 are associated together in any suitable manner. As used herein, the term "associated" encompasses configurations whereby the topsheet 38 is directly joined to the backsheet 43 by affixing the topsheet 38 directly to the backsheet 42, and configurations whereby the topsheet 38 is indirectly joined to the backsheet 42 by affixing the topsheet 38 to intermediate members which in turn are affixed to the backsheet 42. In a preferred embodiment, the topsheet 38 and the backsheet 42 are joined directly to each other in the crotch region 26 in the diaper periphery 28 and indirectly to each other in the waist regions by attachment means such as an adhesive or any other attachment means as is known in the art. For example, a uniform continuous layer of adhesive, a patterned layer of adhesive, an array of separate lines or spots of adhesive, or a network of adhesive filaments such as shown in the above referenced U.S. Pat. No. 4,573,986 may be used.

Tape tab fasteners 54 are typically applied to the back waist region 24 of the diaper 20 to provide a fastening means to hold the diaper on the wearer. The tape tab fasteners 54 can be any of those well known in the art, such as the fastening tape disclosed in U.S. Pat. No. 3,848,594 entitled "Tape Fastening System for Disposable Diaper" which issued to Kenneth Barclay Buell on Nov. 19, 1974, and which is incorporated herein by reference. These tape tab fasteners 54 or other diaper fastening means, such as pins, snaps or velcro fasteners, are typically applied near the top edge of the diaper in its "in-use" configuration.

The elastically contractible leg cuffs 56 are disposed adjacent the periphery 28 of the diaper 20, preferably along each longitudinal edge 30 in at least the crotch region 26 so that the leg cuffs 56 tend to draw and hold the diaper 20 against the legs of the wearer. While the leg cuffs may comprise any of several means as are well known in the diaper art, a particularly preferred leg cuff construction comprises a flexible side flap 58 and one or more flap elastic members 60, as is described in detail in the hereinbefore referenced U.S. Pat. No. 3,860,003. In addition, a method and apparatus suitable for manufacturing a disposable diaper having elastically contractible leg cuffs 56 are described in U.S. Pat. No. 4,081,301 entitled "Method and Apparatus for Continuously Attaching Discrete, Stretched Elastic Strands to Predetermined Isolated Portions of Disposable Absorbent Articles" which issued to Kenneth Barclay Buell on Mar. 28, 1978, and which patent is incorporated herein by reference.

The side flap 58 should be highly flexible and thus contractible so that the flap elastic members 60 may gather the side flap 58 to provide a leg cuff 56 about the wearer. The side flaps 58 are that portion of the diaper 20 between the periphery 28 and the side edges 46 of the absorbent core 44. Thus, in a preferred embodiment of the present invention as shown in FIG. 2, the side flaps 58 are formed from and along the side edges 46 of the absorbent core 44 of the diaper 20 by the topsheet 38 and the backsheet 42 in at least the crotch region 26.

The flap elastic members 60 are operatively associated with the side flaps 58 in an elastically contractible condition so that in a normally unrestrained configuration, the flap elastic members 60 effectively contract or gather the side flaps 58. As used herein, the term "operatively associated" refers to two or more components which act together. The flap elastic members 60 can be secured to the side flaps 58 in an elastically contractible condition in at least two ways. For example, the flap elastic members 60 may be stretched and secured to the side flaps 58 while the side flaps 58 are in an uncontracted condition. Alternatively, the side flaps 58 may be contracted, for example by pleating, and the flap elastic members 60 secured to the contracted side flaps 58 while the flap elastic members 60 are in their relaxed or unstretched condition.

In the embodiment illustrated in FIG. 2, the flap elastic members 60 extend essentially the entire length of the side flaps 58 in the crotch region 26 of the diaper 20. Alternatively, the elastic members 60 may extend the entire length of diaper 20, or any other length suitable to provide an elastically contractible leg cuff 56. The length of the flap elastic members 60 is dictated by the diaper's design.

The flap elastic members 60 may be affixed to the diaper 20 in any of several ways which are well known in the art. For example, the flap elastic members 60 may be ultrasonically bonded, heat/pressure sealed into the diaper 20 using a variety of bonding patterns or the elastic members 60 may simply be glued to the diaper 20. As shown in FIG. 3, the flap elastic members 60 are operatively associated with the side flaps 58 by securing them to the side flaps 58 with an elastic attachment means 86. The elastic attachment means 86 should be flexible and of sufficient adhesiveness to hold the flap elastic member in its stretched condition. The elastic attachment means 86 herein are preferably glue beads made of hot melt adhesives such as marketed by Findley Adhesives Incorporated, Elm Grove, Wis. as Findley Adhesives 581. A more detailed description of the manner in which the flap elastic members 60 may be positioned and secured to the diaper 20 can be found in U.S. Pat. No. 4,253,461 entitled "Absorbent Brief" which issued to Strickland and Visscher on Mar. 3, 1981, and the hereinbefore referenced U.S. Pat. No. 4,081,301 issued to Buell, both of which are incorporated herein by reference.

One flap elastic member 50 which has been found to be suitable is an elastic strand having a cross-section of about 0.18 mm by about 1.5 mm and made from natural rubber as available from Easthampton Rubber Thread Company of Stewart, Va., under the trademark L-1900 Rubber Compound. Other suitable flap elastic members 60 can be made from natural rubber, such as an elastic thread having a cross section of about 0.43 mm (0.017 inches) by about 0.48 (0.019 inches) sold under the tradename rubber compound by Fulflex Company of Scotland, N.C. The flap elastic member 60 may also comprise any heat shrinkable elastic material as is well known in the art. Other suitable flap elastic members 60 may comprise a wide variety of materials as are well known in the art including elastomeric films such as Kraton, polyurethane films, elastomeric foams, ethylene propylene-dimonomers and formed elastic scrim.

In addition, the flap elastic members 60 may take a multitude of configurations. For example, the width of the flap elastic members 60 may be varied from about 0.25 mm (0.01 inches) to about 25 mm (1.0 inch) or more; the flap elastic members 60 may comprise a single strand of elastic material or may comprise several parallel or non-parallel strands of elastic material; or the flap elastic members 60 may be rectilinear or curvilinear.

A waistshield 62 is provided at either or preferably both of the front waist region 22 and the back waist region 24 of the diaper 20. In the description that follows, reference will be made to a waistshield 62 positioned in each of the front waist region 22 and the back waist region 24 of the diaper 20 although a waistshield 62 may be provided only in one of the waist regions.

The waistshield 62 serves as a barrier member intended to prevent premature leakage of the liquid absorbed by the absorbent core 44 from the end edges 32 of the diaper 20. U.S. Pat. No. 4,578,071 entitled "Disposable Absorbent Article Having an Improved Liquid Migration Resistant Perimeter Construction", which issued to Kenneth Barclay Buell on Mar. 25, 1986, and U.S. Pat. No. 4,681,580 entitled "Disposable Diapers with Unitary Waistshield and Elastically Expandable Waistband", which issued to George S. Reising and Jerry L. Dragoo on July 21, 1987, both of which are incorporated herein by reference, describe preferred embodiments of waistshields 62 disposed along the end edges 32 of the diaper 20.

While the waistshield 62 may be a unitary part of the backsheet 42, it is preferably a separate element which may be affixed to the backsheet 42 and made integral therewith. The waistshield 62 is preferably manufactured from a thin, flexible, liquid impermeable material such as polyethylene or polypropylene film. As used herein, the term "unitary" refers to a waistshield 62 and a backsheet 42 which are a single piece of material that is neither divided nor discontinuous. The term "integral" refers to a waistshield 62 which is a discrete separate element affixed to the backsheet 42. The term "liquid impermeable" includes materials which retard the flow of liquid through the thickness of the material in at least one direction.

Materials similar to those used for the backsheet 42 are generally suitable for use as the waistshield 62. A preferred film for use as the waistshield 62 has a sheet tensile strength of at least about 1 pound per inch of width (180 gm/cm of width) in the machine direction of the waistshield and a sheet tensile strength of at least about 0.5 pounds per inch of width (90 gm/cm of width) in the cross-machine direction of the waistshield 62, thereby providing the diaper 20 with improved structural integrity when the waistshield 62 is placed at the end edges 32, especially during fitting and placement of the diaper 20 with improved structural integrity when the waistshield 62 is placed at the end edges 32, especially during fitting and placement of the diaper 20 on the wearer. In addition, a most preferred film for use as the waistshield 62 has a surface energy of at least about 30 dynes/sq. cm. In a preferred embodiment, a heat sealable film such as manufactured by Dow Chemical Company of Midland, Mich. and marketed under the tradename CUF-804 can be used for the waistshield 62.

Referring to FIG. 2, it can be seen that the waistshield 62 has an inward portion 96 and an outward portion 97. The inward portion 96 is interposed between the topsheet 38 and the absorbent core 44 extending from a barriered core edge segment (each portion of the end edge 45 of the absorbent core 44 that is provided with a waistshield 62 is designated a barriered core edge segment) generally toward the center of the absorbent core 44 a distance sufficient to provide protection against leakage of liquid from the portion of the barriered core edge segment. The outward portion 97 of the waistshield 62 extends from the barriered core edge segment toward the end edge 32 and generally provides protection against leakage of liquid from the barriered core edge segment. In the preferred embodiment shown in FIG. 2, the outward portion 97 has an end which is preferably affixed to the backsheet 38 thereby capping the barriered core edge segment. In this preferred embodiment, a peripheral seam (not shown) such as an adhesive is used to affix the waistshield 62 directly to the backsheet 42.

As is shown in FIGS. 1 and 2 the topsheet 38 also preferably has liquid migration resistant segments 98 corresponding to each waistshield 62. The liquid migration resistant segments 98 comprise a compacted portion which alters the flow pattern of liquid as the liquid moves from the point of discharge toward the edges of the diaper 20. The desired effect of the compacted portion may be achieved in many ways such as by filling the inner voids of the compacted portions with adhesive or other liquid impermeable material. A more detailed description of the liquid migration resistant segments 98 can be found in the hereinbefore referenced U.S. Pat. No. 4,578,071 issued to Kenneth Barclay Buell which is incorporated herein by reference. In a preferred embodiment, the compacted portion is compressed or densified relative to the other portions of the topsheet 38 and comprises a multiplicity of bands which define reservoirs therebetween.

A pair of floating inner cuffs 64 extend longitudinally along the diaper 20 in at least the crotch region 26 to provide enhanced leakage prevention and enhanced fit. Thus, a floating inner cuff 64 is disposed in each side of the diaper 20, preferably inboard of the flap elastic members 60, and most preferably between the flap elastic members 60 and the longitudinal centerline 36 of the diaper 20. Of course, a multiplicity of floating inner cuffs 64 may be produced at various portions of the diaper 20 where it is desired to reduce leakage. The floating inner cuffs 64 each preferably comprise a cuff layer 66, a base layer 67, a first seam 68, a central seam 70, an unadhered stand-up portion 72 of the cuff layer 66 between the first seam 68 and the central seam 70, and a central elastic member 74. While the floating inner cuff 64 preferably comprises the above elements, it should be understood that the floating inner cuff 64 may have different configurations wherein elements are added or the first seam 68 and/or the central seam 70 are omitted entirely.

The cuff layer 66 is a flexible member that preferably provides a comfortable layer between the central elastic member 74 and the body of the wearer. The cuff layer 66 may be manufactured from a wide variety of materials. The materials used to manufacture the cuff layer 66 are preferably compliant, soft feeling, and non-irritating to the wearer's skin since the cuff layer 66 lays against the skin of the wearer. The cuff layer 66 may be manufactured from a wide range of materials such as porous foams, apertured films, natural fibers (e.g., wood or cotton fibers) or from a combination of natural and synthetic fibers and from a number of manufacturing techniques such that the cuff layer 66 may be woven, nonwoven, spunbonded, carded or the like. In general, any material which is suitable for use as the topsheet 38 is also suitable for use as the cuff layer 66.

A particularly preferred cuff layer 66 comprises in at least the crotch region 26 a portion of the topsheet 38 and in the front waist region 22 and the back waist region 24 a combination of the topsheet 38 and the waistshield 62.

While the cuff layer 66 may be one or more separate members secured to the diaper 20 and made integral therewith to form distinct floating inner cuffs 64, the cuff layer 66 preferably comprises a portion of the topsheet 38 (i.e., the cuff layer 66 and the topsheet 38 are the same piece of material). While the cuff layer 66 in at least the crotch portion 26 in the preferred embodiment comprises a portion of the topsheet 38, it should be understood that the cuff layer 66 may comprise one or more layers or materials such as a topsheet and a wicking layer, a topsheet and the tissue layer enwrapped about the absorbent core, the topsheet and the waistshield such as the configuration of the cuff layer 66 in the front waist region 22 and the back waist region 24, or any other combination of layers or materials.

The base layer 67 underlays the cuff layer 66 and forms the base of the floating inner cuff 64. The bas layer 67 is thus that portion of the diaper 20 positioned below the cuff layer 66 and the central elastic members 74. While the base layer 67 may comprise a separate element, such as a nonwoven layer of material secured to the diaper 20, the base layer 67 is preferably formed from the portion of the diaper 20 underlying the cuff layer 66. Thus, as shown in FIGS. 3 and 4, the base layer 67 preferably comprises both the absorbent core 44 and the portion of the backsheet 42 extending beyond the side edges 46 and the end edges 45 of the absorbent core 44.

The first seam 68 secures a portion of the cuff layer 66 to the base layer 67, preferably the backsheet 42, in at least the crotch region 26. Thus, the first seam 68 preferably comprises an attachment means to secure a portion of the cuff layer 66, preferably an edge portion of the cuff layer 66, to the base layer 67. The first seam 68 may comprise any of a number of known attachment means such as adhesives, ultrasonic bonding or heat/pressure sealing. Preferably, the first seam 68 is a glue bead of hot melt adhesive such as is marketed by Findley Adhesives, Inc., Elmgrove, Wis. as Findley Adhesives 990374.

The first seam 68 may be positioned anywhere in the diaper 20 between the longitudinal edge 30 and the longitudinal centerline 36, for example, adjacent the longitudinal edge 30. The first seam 68 is preferably positioned adjacent the leg cuffs 56 and more preferably inboard of the flap elastic members 60 to provide a pair of floating inner cuffs 74 in the center portion of the diaper 20. Most preferably, the first seam 68 is positioned between the flap elastic members 60 and the side edge 46 of the absorbent core 44 in each side of the diaper 20 so that the first seam 68 is positioned outwardly from the absorbent core 44.

A central seam 70 secures a portion of the cuff layer 66 to the base layer 67, preferably the absorbent core 44, in at least the crotch region 26. Thus, the central seam 70 preferably comprises an attachment means to secure a portion of the cuff layer 66, preferably an edge portion of the cuff layer 66, to the base layer 67. The central seam 70 may comprise any of a number of known attachment means such as adhesives, ultrasonic bonding or heat/pressure sealing. In particular, the central seams 70 preferably comprise a plurality of hot melt adhesives filaments. This open pattern network of filaments of adhesive that is used to secure the cuff layer 66 to the base layer 67 (i.e., the topsheet 38 to the absorbent core 44) is discussed in more detail in U.S. Pat. No. 4,573,986 entitled "Disposable Waste-Containment Garment" which issued to James A. Minetola and David R. Tucker on Mar. 4, 1986, and which is incorporated herein by reference. Such a network of filaments of hot melt adhesive provides core integrity without unduly negatively affecting absorbency or softness of the absorbent core 44.

The central seam 70 is spaced inboard of the first seam 68 to provide an unadhered stand-up portion 72 between the first seam 68 and the central seam 70. Preferably, the central seams 70 are positioned adjacent the longitudinal centerline 36 of the diaper 20 to provide a floating inner cuff 64 positioned in the center portion of the diaper 20. While the central seams 70 of each floating inner cuff 64 may comprise separate stripes, patterns or networks of adhesive, the floating inner cuffs 64 preferably have a common central seam positioned in the center portion of the diaper 20 in at least the crotch region 26 as shown in FIGS. 2 and 3. This common central seam allows more even distribution of the adhesive in the center portion of the diaper 20 and ease of manufacture in that two distinct central seams need not be separately formed.

The unadhered stand-up portion 72 of the floating inner cuff 64 is that portion of the cuff layer 66 disposed between the first seam 68 and the central seam 70 that is unadhered to the base layer 67 in at least the crotch region 26. Since the stand-up portion 72 is unadhered to the base layer 67, this portion of the cuff layer 66 is free to move relative to the base layer 67 so that as the central elastic member 74 stands up and is spaced away from the base layer 67, the cuff layer 66 also stands up and is spaced away from the base layer 67. Thus, the unadhered stand-up portion 72 forms the ridge 88 of the floating inner cuff 64 so as to reduce leakage.

The central elastic members 74 provide a restoring force to keep the crotch region 26 of the diaper 20 fitted against the wearer's body to thereby reduce leakage, improve the positioning of the cuff layer 66 relative to the genital area of the wearer, "float" to a wearer's leg crease to give the diaper 20 a tighter sustained fit, and provide a barrier to leakage when they are free standing by causing the unadhered stand-up portion 72 of the cuff layer 66 to be spaced away from the base layer 67 so as to provide a ridge 88.

As shown in FIGS. 1 and 2, the central elastic members 74 extend longitudinally along the diaper 20 in a spaced apart relation. The central elastic members 74 are operatively associated in the floating inner cuff 64 in an elastically contractible condition so that in a normally unrestrained configuration, the central elastic members 74 effectively contract or gather the unadhered stand-up portion 72 of the cuff layer 66, preferably the topsheet 38, so as to provide a ridge 88 and to be floating to provide a better fit. The central elastic members 74 can be secured to the diaper 20, preferably to the waistshield 62 and the absorbent core 44, in an elastically contractible condition in at least two ways. For example, the central elastic members 74 may be stretched and secured to the floating inner cuff 64. Alternatively, the diaper 20 may be contracted, for example by pleating, and the central elastic members 74 secured to the contracted diaper while they are in their unrelaxed or unstretched condition.

In the embodiment illustrated in FIGS. 1 and 2, the central elastic members 74 extend essentially the entire length of the absorbent core 44 of the diaper 20. Alternatively, the central elastic members 74 may extend the entire length of the diaper 20, or any other length suitable to provide the functions described herein. The length of the central elastic members 74 is dictated by the diaper's design.

The central elastic members 74 are positioned along the unadhered stand-up portion 72 of the cuff layer 66, preferably subjacent the unadhered stand-up portion 72, to allow the cuff layer 66 to stand-up and be spaced away from the base layer 67. Thus, each central elastic member 74 is positoned between the first seam 68 and the central seam 70 and preferably between the cuff layer 66 and the base layer 67. As used herein, the term "subjacent" is used to denote that the central elastic member 74 is directly or indirectly positioned below the unadhered stand-up portion 72 of the cuff layer 66. Thus, the central elastic member 74 may be in contact with the cuff layer 76 (directly subjacent) or have intermediate members, elements or layers such as a foam layer to prevent red marking by the central elastic member, positioned between the central elastic member 74 and the cuff layer 66 (indirectly subjacent). In a preferred embodiment, the central elastic members are positioned directly subjacent the cuff layer 66 in at least the crotch region 26.

As is shown in FIG. 2, the central elastic members 74 each have a pair of affixed portions 76 and an unaffixed portion 78 between the pair of affixed portions 76. The affixed portions 76 are affixed to the floating inner cuff 64, preferably to both the cuff layer 66 and the base layer 67. While the unaffixed portion 78 may be permanently affixed to the cuff layer 66 or releasably affixed to the cuff layer 67 and/or the base layer 67, the unaffixed portion 78 of each central elastic member 74 is preferably not affixed to the cuff layer 66, the base layer 67 or any structure of the diaper 20. The affixed portions 76 may be affixed to the diaper 20 in any of several ways which are known in the art. For example, the central elastic members 76 may be ultrasonically bonded, heat/pressure sealed using a variety of bonding patterns, stitched or weaved through a small portion of the topsheet to constrain lateral movement, or adhesively secured by an elastic attachment means 80 such as is shown in FIG. 4. The elastic attachment means 80 should be flexible and a sufficient adhesiveness to hold the central elastic member 74 in its stretched condition. The elastic attachment means 80 herein are preferably glue beads made of hot melt adhesive such as marketed by Findley Adhesives, Inc., Elmgrove, Wis. as Findley Adhesives 581. A more detailed description of the manner in which the central elastic members 74 may be positioned and secured to the diaper 20 can be found in the hereinbefore referenced U.S. Pat. No. 4,253,461 issued to Strickland and Visscher and U.S. Pat. No. 4,081,301 issued to Buell, both of which are incorporated herein by reference.

A central elastic member 74 which has been found to be suitable is an elastic strand having a cross-section of about 0.43 millimeters by about 0.48 millimeters and made from natural rubber as available from Fulflex Company of Scotland, N.C. The central elastic members 74 may also comprise any heat-shrinkable, heat-activated, or liquid or urine-activated elastic material as are well known in the art. Other suitable central elastic members 74 may comprise a wide variety of materials as are known in the art including elastomeric films such as Kraton, polyurethane films, elastomeric foams, ethylene-propylene dimonomers, and formed elastic scrim.

In addition, the central elastic members 74 may take a multitude of configurations. For example, the width of the central elastic members 74 may be varied; the central elastic members 74 may comprise a single strand of elastic material or comprise several parallel or non-parallel strands of elastic material; or the central elastic members 74 may be rectilinear or curvilinear. As shown in FIG. 2, each of the central elastic members 74 are longitudinally spaced from each other so as to provide a central portion between the central elastic members 74. Further, the central elastic members 74 are preferably positioned so that one is placed on either side of the longitudinal centerline 36 of the diaper 20. In particularly preferred embodiments, the central elastic members 74 are equidistantly spaced from the longitudinal centerline 36 to provide optimal fit adjacent the leg creases of the wearer.

In a preferred embodiment as shown in FIG. 2, the affixed portions 76 of the central elastic members 74 are disposed in both the front waist region 22 and the back waist region 24 of the diaper 20 in the front zone 82 and the back zone 84, respectfully. While the front zone 82 and the back zone 84 may be differently configured such that they have different lengths or are disposed in different areas of the diaper 20, the front zone 82 and the back zone 84 preferably have the same length and are disposed in the same area in each of the waist regions. Preferably, the front zone 82 and the back zone 84 are disposed so that the central elastic member 74 is at least partially bonded to the waistshield 62. Most preferably, the front zone 82 and the back zone 84 extend from the inward portion 96 of the waistshield 62 adjacent the end edge 45 of the absorbent core 44 toward the center of the absorbent core 44 to beyond the edge of the waistshield 62 a distance sufficient to firmly secure the central elastic member 74 to the floating inner cuff 64. Thus, the fixed portions 76 of the central elastic members 74 are secured both to the waistshield 62 and the absorbent core 44 and to the topsheet 38 and the absorbent core 44.

FIGS. 1 and 4 show that the diaper 20 also preferably comprises a stiffening means 90 for adding stiffness to a waist region of the diaper 20 to prevent the central elastic members 74 from pulling the waist region down so as to present gaps between the skin of the wearer and the diaper 20. The stiffening means 90 may be a separate member secured to the backsheet 38 and made integral therewith or may be a unitary part of the backsheet 42. The stiffening means 90 is preferably a separate member secured to the outside surface 92 of the backsheet 42 in only the front waist region 22 so as to provide a refastenable tape member for the tab tape fastener 54 of the diaper 20. The stiffening means 90 may comprise any of several elements or members as are known in the art for stiffening the backsheet 38 such as beads or lines of adhesive; sheets of material; or inherent properties of the backsheet 38 that stiffen when acted upon by a stimulus such as irradiation. A preferred stiffening means is a sheet of biaxially oriented polypropylene material.

The stiffening means 90 is also preferably provided with indicia means 100 for aiding an individual fitting the diaper 20 to a wearer to obtain optimal waist fit and leg opening fit. The indicia 100 may be any type of lines, patterns, ornamental designs, symbols, script, color codes, or other markings which have the capability, either inherently or with additional denotation, to aid an individual fitting the diaper to the wearer to promptly locate the desired affixation point for a particular tape tab fastener. Such indicia means are more generally described in U.S. Pat. No. 4,662,875 entitled "Absorbent Article" which issued to Dennis O.Hirotsu and Anthony J. Robertson on May 5, 1987, and which is incorporated herein by reference. Indicia means 100 of the present invention are preferably a combination of different geometric shapes and objects such as a pattern of bears, balloons, and suns.

The diaper 20 is applied to a wearer by positioning the back waist region 24 under the wearer's back and drawing the remainder of the diaper 20 between the wearer's legs so that the front waist region 22 is positioned across the front of the wearer. The ends of the tape tab fasteners 54 are then secured preferably to areas of the stiffening means 90 of the diaper 20 by utilizing the indicia means 100 to properly fit the diaper 20 to the wearer. In this manner, the floating inner cuffs 64 and the central elastic members 74 should be disposed adjacent the leg creases of the wearer and should provide the dispositions and functions described herein.

Basically, without intending to limit the present invention, the present invention is an absorbent article that is especially leakage resistant against both urine and loose fecal material. The improved containment characteristics are believed to be achieved in the following manner. As the diaper 20 is applied to the wearer, the central elastic members 74 provide a restoring force to maintain the crotch fit of the diaper 20 against the wearer's body. This secure fit prevents leakage along the edges of the diaper 20 since the topsheet 38 is positioned adjacent the point of discharge of urine and fecal material. The central elastic members 74 also seek the leg crease of the wearer and provide a tighter and sustained fit as they move and adapt to the wearer's shape. Thus, as loose fecal material or urine (hereinafter referred to as surface material) is discharged onto the topsheet 38, the surface material flows or floats on the top surface of the topsheet 38. The surface material moves from the point of discharge toward the longitudinal edges 30 of the diaper 20, especially along channels or creases formed in the topsheet during use. Surface material will contact the ridges 88 formed by the floating inner cuffs 64. In normal use, the ridges 88 will block or inhibit movement of the surface material beyond the ridges 88 and cause the surface material to stay within the bounds of the diaper 20 because surface material would have to flow up and over the ridges 88, which direction is substantially directly against the force of gravity when the wearer is in an upright position, in order to flow beyond the ridges 88. Since the central elastic members 74 are free standing or floating in the crotch region 26 and seek the leg creases of the wearer, the floating inner cuffs 64 provide an improved sustained fit that also inhibits movement of surface material beyond the floating inner cuffs 64. Improved containment is also achieved even if such surface material should flow beyond the floating inner cuffs 64, because the surface material is further retarded from leaking out of the diaper 20 by the leg cuffs 56 as they draw and gather the side flaps 58 about the legs of the wearer.

In an alternative embodiment of the present invention, each of the floating inner cuffs has a common cuff layer defined by at least the portion of the topsheet disposed between the flap elastic members on each side of the diaper. Additionally, each of the floating inner cuffs does not comprise the control seam such that the topsheet comprises an unadhered stand-up portion across its entire width between the first seams. Thus, the entire portion of the topsheet between the first seams may stand-up and be spaced away from the base layer, preferably the absorbent core, in at least the crotch region. Since the topsheet is allowed to be spaced away from the absorbent core by the gathering action of the central elastic members in the area where body elastic members in the area where body exudates are likely to be deposited onto the topsheet, it is believed that liquids may be more quickly acquired into the diaper because the void area created immediately below the surface of the topsheet creates a large capillary difference such that liquids would be quickly drawn into the diaper and because the topsheet diffuses the high velocity of body exudates.

In a further alternative embodiment of the present invention, the unaffixed portion of each of the central elastic members are affixed to the cuff layer, preferably the topsheet, so that the cuff layer and the central elastic member closely cooperate to form the floating inner cuffs. Thus, in this alternative embodiment the central elastic member may be affixed to either the top surface of the cuff layer or to the bottom surface of the cuff layer (subjacent the cuff layer), although the central elastic member is preferably positioned subjacent the cuff layer. By affixing the central elastic member to the cuff layer, the central elastic member is inhibited from laterally floating along the cuff layer such that the central elastic members is fixedly laterally positioned within the floating inner cuff.

As an alternative to permanently affixing the central elastic member to the cuff layer, the central elastic member may be releasably affixed to the cuff layer by an attachment means that releases the central elastic member from the cuff layer, for example, when the diaper is stretched prior to positioning it upon the wearer or by a liquid or urine-activated adhesive that dissolves or loses its adhesiveness when liquids come into contact with the adhesive, such that the central elastic member would be free to float within the floating inner cuff only after the diaper has been fitted to the wearer or body exudates have been voided into the diaper. Thus, the floating inner cuffs would have a dynamic fit.

In a still further alternative embodiment, the central elastic members may comprise a user-activated, heat-activated, or liquid or urine-activated elastic member that is manufactured from a material that becomes elastically contractible only when stretched prior to wearing or when contacted with heat, liquids or urine such that the floating inner cuffs are dynamically activated.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An integral disposable absorbent article having a front waist region, a back waist region, and a crotch region disposed between the front waist region and the back waist region, the absorbent article comprising:

an absorbent core having a garment facing surface, a body facing surface, and a pair of side edges;

a backsheet associated with said absorbent core on said garment facing surface; a continuous topsheet associated with said absorbent core on said body facing surface of said absorbent core;

a side flap extending outwardly from and along each side edge of said absorbent core in at least the crotch region;

a flap elastic member operatively associated with each of said side flaps in an elastically contractible condition; and a floating inner cuff longitudinally extending along the absorbent article in at least the crotch region in each side of the absorbent article, each of said floating inner cuffs comprising:

a cuff layer;

a base layer underlaying said cuff layer;

a first seam for securing a portion of said cuff layer to said base layer;

a central seam spaced inboard from said first seam for securing a portion of said cuff layer to said base layer;

said cuff layer having an unadhered stand-up portion positioned between said first seam and said central seam that is unadhered to said base layer; and a central elastic member operatively associated with said floating inner cuff in an elastically contractible condition and positioned subjacent said unadhered stand-up portion of said cuff layer, said central elastic member comprising a pair of affixed portions and an unaffixed portion between said pair of affixed portions, said pair of affixed portions being affixed to said cuff layer and said base layer and said unaffixed portion being unaffixed to said base layer and said cuff layer so that said central elastic member may float in the crotch region of the absorbent article so as to optimize fit of said floating inner cuff, wherein said unaffixed portion is positioned in at least the crotch region of the absorbent article so that said unaffixed portion causes said unadhered stand-up portion of said cuff layer to stand-up and be spaced away from said base layer to form a ridge that enhances leakage prevention.

2. The absorbent article of claim 1 wherein said floating inner cuffs have a common central seam.

3. The absorbent article of claim 2 wherein said central seam comprises a plurality of adhesive filaments.

4. The absorbent article of claim 1 wherein said cuff layer comprises a portion of said topsheet.

5. The absorbent article of claim 1 wherein said first seam is positioned inboard of said flap elastic member.

6. The absorbent article of claim 1 wherein said cuff layer comprises a portion of said topsheet.

7. The absorbent article of claim 1 wherein said floating inner cuffs have a common central seam.

8. The absorbent article of claim 7 wherein said cuff layer comprises a portion of said topsheet.

9. The absorbent article of claim 8 additionally comprising a stiffening means positioned on said backsheet in the front waist region of the absorbent article.

10. The absorbent article of claim 9 wherein said central elastic member comprises an elastic strand.

11. The absorbent article of claim 10 wherein said first seam is positioned inboard of said flap elastic member.

12. The absorbent article of claim 11 wherein said central seam comprises a plurality of adhesive filaments.

13. The absorbent article of claim 12 wherein said side flap is formed from the extension of said backsheet and said topsheet beyond the side edges of the absorbent core.

14. The absorbent article of claim 13 wherein said central elastic members are spaced apart so that one is disposed in each side of the longitudinal centerline of the absorbent article.

15. The absorbent article of claim 14 wherein said central elastic members are equidistantly disposed from the longitudinal centerline of the absorbent article.

16. The absorbent article of claim 15 wherein said gasketing cuffs each comprises a plurality of flap elastic members.

17. The absorbent article of claim 16 additionally comprising a waistshield positioned between said absorbent core and said topsheet in each of the front waist region and the back waist region.

18. The absorbent article of claim 17 wherein each of said waistshields are positioned between said topsheet and said central elastic members.

19. The absorbent article of claim 18 wherein said stiffening means is positioned on the outside surface of said backsheet.

20. The absorbent article of claim 19 additionally comprising indicia means positioned on said stiffening means.

21. The absorbent article of claim 20 wherein said first seam is positioned between said flap elastic member and said side edge of said absorbent core.

22. The absorbent article of claim 1 additionally comprising a stiffening means positioned on said backsheet in the front waist region of the absorbent article.

23. The absorbent article of claim 22 wherein said stiffening means is positioned on the outside surface of said backsheet.

24. The absorbent article of claim 23 additionally comprising indicia means positioned on said stiffening means.

25. The absorbent article of claim 1 wherein said central elastic member comprises an elastic strand.

* * * * *

UNITED STATES PATENT AND TRADEMARK OFFICE
CERTIFICATE OF CORRECTION

PATENT NO. : 4,808,177

DATED : February 28, 1989

INVENTOR(S) : Thomas A. DesMarais, Robert H. Siegfried

It is certified that error appears in the above-identified patent and that said Letters Patent is hereby corrected as shown below:

Column 3, Line 68, "and" should read ---an---.

Column 4, Line 2, "classic" should read ---elastic---.

Column 4, Line 36, "389" should read ---38---.

Column 4, Line 50, "these" should read ---those---.

Column 5, Line 7, "86 to to form" should read ---86 to form---.

Column 6, Line 49, "of hydrophobic" should read ---of natural and synthetic fibers. Preferably, it is made of a hydrophobic---.

Column 10, Line 21, "50" should read ---60---.

Column 11, Line 4, "as polyethylene" should read ---as a polyethylene---.

Column 12, Line 12, "produced" should read ---provided---.

Column 12, Line 61, "bas" should read ---base---.

Column 16, Line 19, between "20." and "The", insert ---The stiffening means 90 may comprise any of a number of configurations and materials positioned on the backsheet 42 of the diaper 20.

Column 16, Line 25, "tab tape" should read ---tape tab---.

UNITED STATES PATENT AND TRADEMARK OFFICE
CERTIFICATE OF CORRECTION

PATENT NO. : 4,808,177
DATED : February 28, 1989
INVENTOR(S) : Thomas A. DesMarais, Robert H. Siegfried It is certified that error appears in the above-identified patent and that said Letters Patent is hereby corrected as shown below:

Column 17, Line 40, "control" should read --central--.

Signed and Sealed this

First Day of August, 1989

Attest:

DONALD J. QUIGG

Attesting Officer      Commissioner of Patents and Trademarks